United States Patent [19]

Lebaud et al.

[11] Patent Number: 4,730,493
[45] Date of Patent: Mar. 15, 1988

[54] PROCESS AND DEVICE FOR ULTRASONIC DETECTION OF GAS BUBBLES IN A LIQUID METAL

[75] Inventors: Patrice Lebaud, Clamart; Gérald Isnardon, Courbevoie, both of France

[73] Assignee: Novatome, Courbevoie, France

[21] Appl. No.: 913,294

[22] Filed: Sep. 30, 1986

[30] Foreign Application Priority Data

Sep. 30, 1985 [FR] France ................ 85 14466

[51] Int. Cl.$^4$ .............................................. G01H 3/12
[52] U.S. Cl. ...................................... 73/599; 376/340
[58] Field of Search .................. 73/599, 590, 600, 627, 73/628, 629; 376/340

[56] References Cited

U.S. PATENT DOCUMENTS 3,057,189 10/1962 Joy ......................................... 73/629
3,779,070 12/1973 Cushman et al. ................. 73/628 X Primary Examiner—Jerry W. Myracle
Attorney, Agent, or Firm—Pollock, Vande Sande & Priddy

[57] ABSTRACT

An ultrasonic beam is sent into liquid metal from a transmitting point (3) outside the enclosure (1) containing the liquid metal, the beam is detected outside the enclosure (1) after it has passed through the liquid metal, the amplitude of the ultrasonic waves detected is compared with the amplitude of the transmitted ultrasonic waves and the attenuation of the ultrasounds produced by the passage through the liquid metal which may contain gas bubbles (2) is determined. The device comprises a wave guide (4) metallurgically connected to the enclosure (1). A processing unit (10) connected to the ultrasonic transducers (3, 6) measures the attenuation.

5 Claims, 12 Drawing Figures

PROCESS AND DEVICE FOR ULTRASONIC DETECTION OF GAS BUBBLES IN A LIQUID METAL

FIELD OF THE INVENTION

The invention relates to a process and a device for the ultrasonic detection of gas bubbles in a liquid metal contained in an enclosure.

BACKGROUND OF THE INVENTION

Liquid metals, in particular circulating liquid metals, may contain gas bubbles of more or less large size which are entrained by the liquid in all the parts of the industrial installation where these metals are used. The origin and the nature of these gases may be very diverse, but generally these gases disturb, sometimes in an extremely serious way, the operation of the installation.

In the case of fast neutron nuclear reactors cooled by liquid sodium, the gas contained in the sodium may be hydrogen coming from the steam generator in the case where this generator has a slight leakage, the cooling water being decomposed by the sodium.

This gas may also be argon or another inert gas which acts as an atmosphere covering the sodium and which may be driven by a circulation pump.

This gas may also be constituted by vapor bubbles of the liquid metal produced by the cavitation of a pump.

In the first case, a rapid detection of the hydrogen bubbles is necessary in order to detect a possible leakage in the steam generator which may require, if it is serious, the immediate stoppage of the reactor.

In the second case, it is also desirable to detect the argon bubbles in the cooling sodium of the reactor, since these argon bubbles are liable to reduce to a considerable extent the cooling capacity of the sodium and consequently to result in formation of hot points in the fuel assemblies which have an adverse affect on their behavior in service.

In the third case, these vapor bubbles formed by the cavitation of a pump will, by the implosion effect, result in erosions which adversely affect the life of the apparatus.

Methods are known for detecting gas bubbles, for example, in the case of hydrogen, the diffusion of this hydrogen through a wall in contact on one side with the liquid metal and on the other side with a medium at very low pressure. Such a method is, however, relatively complicated to employ and has a sensitivity which depends on the temperature of the sodium and, above all, a long response time.

Processes are also known for the ultrasonic detection or measurement of foreign bodies in a homogeneous medium. Ultrasounds have, for example, been used for measuring the quantity of vapor in the form of bubbles in water at high temperature and at high pressure contained in an enclosure. This process, however, cannot be transposed to the case of liquid metals, since it employs measurements of the velocity of ultrasounds and requires the presence of ultrasonic transmitters or receivers in the immediate vicinity of, or in contact with, the enclosure enclosing the liquid; this process indeed employs measurements of the time taken by ultrasonic waves to travel in water under pressure which may possibly contain vapor bubbles.

In the case of liquid metals, in particular in the case of liquid sodium for cooling a fast neutron nuclear reactor, the temperature of this liquid metal may reach temperatures much higher than 400° C. which are transmitted to the wall of the enclosure surrounding the metal. Ultrasonic transmitter-receivers which are capable of operating correctly at these temperatures are very expensive and of doubtful reliability.

SUMMARY OF THE INVENTION

An object of the invention is therefore to provide a process for the ultrasonic detection of gas bubbles in a liquid metal contained in an enclosure which is simple and very sensitive, has a very short response time and can be employed for liquid metals at very high temperatures.

For this purpose, the process according to the invention comprises the steps of:

sending an ultrasonic beam in the liquid metal from a transmitting point located at the exterior and at a distance from the enclosure so as to produce the propagation of these ultrasounds in a given length through the liquid metal;

detecting the ultrasonic beam at the exterior at a distance from the enclosure after it has passed through the liquid metal;

comparing the amplitude of the detected ultrasonic waves with the amplitude of the ultrasonic waves transmitted so as to determine the attenuation of the ultrasonic beam produced by the travelling through the liquid metal;

and deducing the presence of gas bubbles in the liquid if the attenuation of the ultrasonic beam exceeds a given threshold either in a continuous manner or by brief pulses.

The invention also relates to a detecting device comprising at least one ultrasonic transducer coupled with the enclosure enclosing the liquid metal through a waveguide metallurgically connected to the enclosure.

BRIEF DESCRIPTION OF THE DRAWINGS

In order that the invention may be more clearly understood, reference will now be made to the accompanying drawings, which show several embodiments of a device according to the invention for detecting gas bubbles in a liquid metal flowing in a conduit.

DESCRIPTION OF PREFERRED EMBODIMENTS

Figure 1:
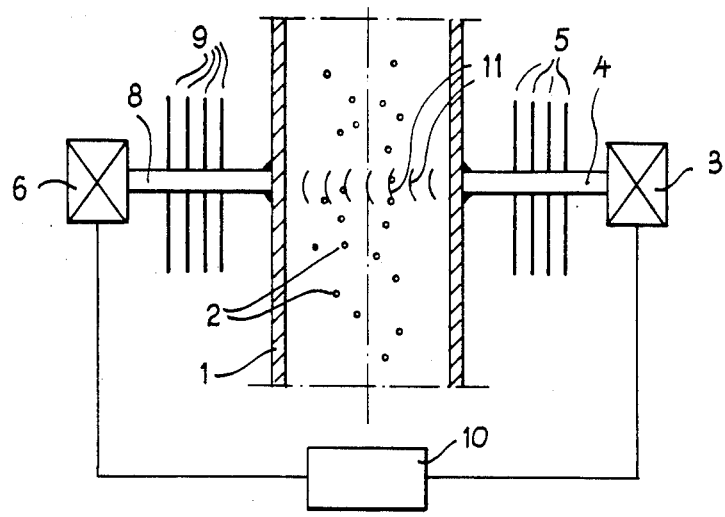
FIG. 1 is a schematic view, partly in section, on the axis of the conduit, of a gas bubble detecting device according to a first embodiment of the invention.

FIG. 1 shows the conduit 1 in which flows the liquid metal which is, for example, secondary sodium of a fast neutron nuclear reactor which may optionally contain and entrain bubbles of hydrogen 2.

The gas bubble detecting device comprises an ultrasonic transmitter 3 coupled by means of a metal bar 4 to the wall of the conduit 1, to which the bar 4 is welded at the end thereof opposed to the end in contact with the ultrasonic transmitter 3. The metal bar 4 is surrounded by cooling fins 5 for evacuating the heat transmitted through the wall of the conduit 1 and thus limiting the temperature of the end of the bar 4 in contact with the transmitter 3.

In the case where the liquid metal is primary sodium, its temperature may indeed reach 650° C., particularly in the case of accidental conditions of operation of the reactor. The remoteness of the transmitter 3 from the wall of the conduit 1 and the presence of fins, enable the temperature of the surface of contact between the transmitter and the wave guide to be limited to a level allowing the use of an ordinary detector. The detecting device also includes an ultrasonic receiver 6 coupled to the wall of the conduit 1 through a metal wave guide 8 welded to the conduit; the latter may be in the extension of the wave guide 4. The wave guide 8 may also include cooling fins 9 for limiting its temperature at the end thereof connected to the ultrasonic receiver 6. A processing unit 10 receives the electrical signals corresponding to the ultrasonic waves transmitted by the transducer 3 and the ultrasonic waves received by the transducer 6. The processing unit 10 permits a comparison of the amplitudes of the signals corresponding to the ultrasonic waves respectively transmitted and received so as to deduce the attenuation undergone by the waves 11 when they are propagated through the liquid metal which may contain gas bubbles 2.

Figure 1B:
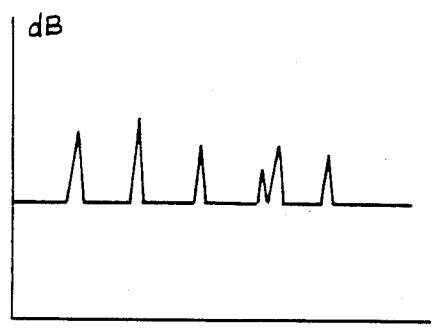
FIG. 1b is a diagram showing the variations over a period of time of the attenuation of the ultrasonic beam in the case of the presence of isolated bubbles in the liquid metal.
Figure 1A:
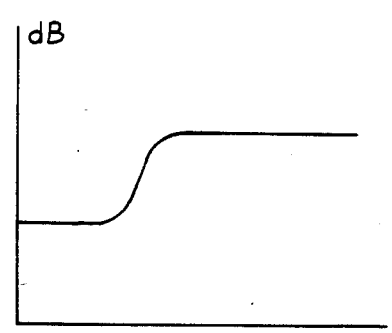
FIG. 1a is a diagram showing the variations over a period of time of the attenuation of the ultrasonic beam employed for the detection of bubbles in the case of a continuous production of bubbles in the liquid metal.

The attenuation of the ultrasonic waves in the liquid metal is considerably increased when the gas bubbles are present in this metal. As can be seen in FIGS. 1a and 1b, the presence of a continuous stream of bubbles results in an increase in the attenuation which is stabilized at a substantially constant value, while a slight presence of isolated bubbles results in a series of brief pulses on the attenuation curve. There is consequently determined the attenuation threshold beyond which there is an effective presence of bubble in the liquid metal. A comparison module integrated in the processing unit 10 permits determining whether the attenuation threshold has been reached. When the attenuation threshold is reached or exceeded, an alarm or display device associated with the processing unit 10 warns the operator in charge of the installation.

In order to achieve an optimum detection of the gas bubbles in liquid sodium, there will be used frequencies usually between 100 kHz and 10 MHz. Indeed, the attenuation in the liquid metal containing gas bubbles depends, to a certain extent, on the frequency of the ultrasonic waves employed and on the size of the existing bubbles. A frequency will therefore be chosen which permits the obtainment of the best possible sensitivity in accordance with the characteristics of the installation, the nature of the gas which may be formed and may be entrained by the liquid metal, and the size of the bubbles which may be formed.

In any case, in the case of sodium circuits of a fast neutron nuclear reactor, the frequency must be chosen distinctly higher than the frequency of this material. In order to satisfy this requirement, there will always be employed waves having a frequency higher than 20 kHz. The detecting process and device according to the invention are extremely sensitive, in particular when the frequency of the ultrasonic waves is suitably chosen. Thus, in liquid sodium flowing in a conduit of a fast neutron nuclear reactor circuit, it was possible to measure attenuations on the order of 6 decibels for gas contents on the order of 5% in the liquid, with ultrasonic waves of a frequency of 500 kHz ; under the same conditions, it was possible to measure attenuations on the order of 20 decibels for gas contents of 7% with ultrasonic waves of a frequency of 2 MHz.

In the case of large-size steam generators of the type of those employed in the Superphenix fast neutron power station, bearing in mind the flows of sodium, it is possible, by means of the detecting process and device according to the invention, to detect leakages of less than 10 g/s of water by measurements of the attenuation of ultrasonic waves by the hydrogen bubbles formed and entrained in the sodium outlet conduit of the steam generator.

Figure 2:
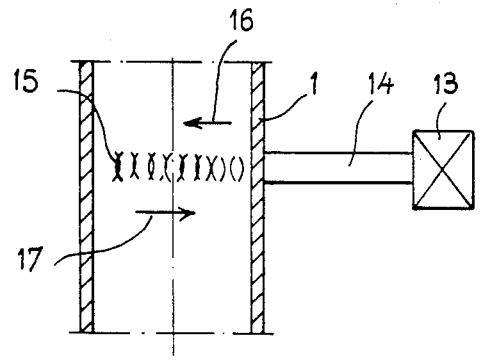
FIG. 2 is a schematic view, partly in section, on the axis of the conduit, of a detecting device according to a second embodiment of the invention.
Figure 4A:
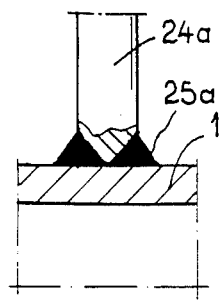
FIGS. 4a, 4b, 4c and 4d are sectional views of the connection zone between the wave guide and the conduit through which the liquid metal passes.
Figure 4B:
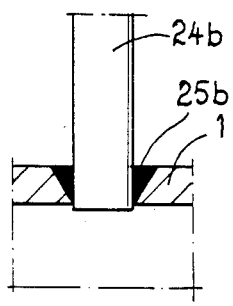
Figure 4C:
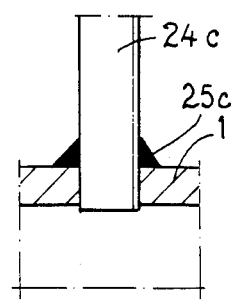
Figure 4D:
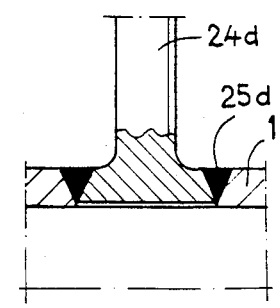

FIG. 2 shows a modification of the detecting device, the transducer 13 being formed by an ultrasonic wave transmitter-receiver unit which both transmits and receives the waves. As before, this transducer 13 is connected to a processing unit (not shown) which measures the attenuation of the waves 15 due to the propagation thereof in the liquid metal which may contain gas bubbles. The waves 15 are propagated first of all in the direction of arrow 16, which is a substantially diametrical direction of the conduit 1, then are reflected by the wall of the conduit 1 opposed to the wave guide 14 and then returned into the wave guide 14 in the direction indicated by arrow 17 which is the same diametrical direction as before. The arrangement shown in FIG. 2 has the advantage of increasing the length of the path of the ultrasounds in the liquid metal and therefore the attenuation and the sensitivity of the detection. It will be understood that the wave guide 14 may be provided with cooling fins as before.

Figure 3:
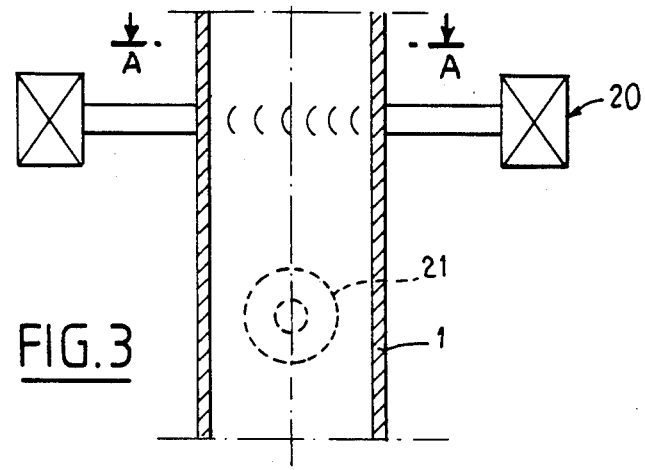
FIG. 3 is a diagrammatic view, with a part in section, on the axis of the conduit, of a detecting device according to a third embodiment of the invention.
Figure 3A:
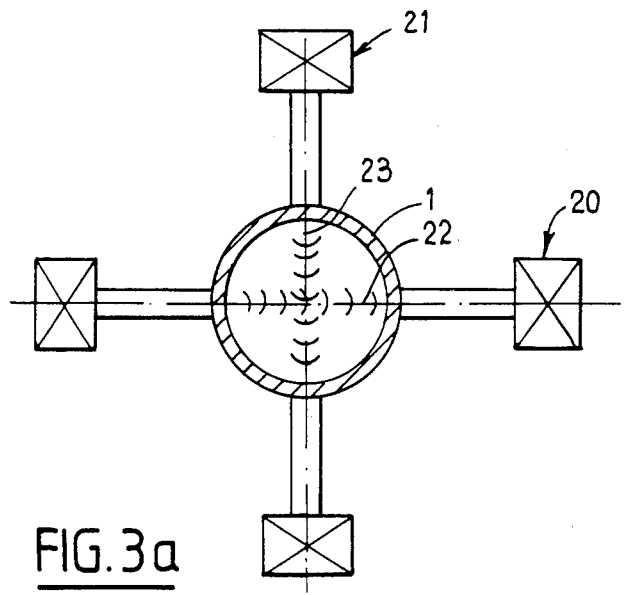
FIG. 3a is a sectional view taken on line A—A of FIG. 3.

There can be seen in FIGS. 3 and 3a an embodiment of the device according to the invention, which is particularly adapted to the case of a conduit having a relatively large diameter (for example exceeding 0.20-0.30 m), which conduit has sudden changes in direction, such as elbows, as is almost always the case in fast neutron nuclear reactor circuits. In the case of a large-diameter conduit having elbows or on which are mounted various apparatus, the concentration of bubbles may indeed essentially vary in the section of the conduit. It is then desirable to measure the attenuation in a plurality of directions of the section, for example in a plurality of diameters and/or in a plurality of regions lengthwise of the conduit. The device shown in FIGS. 3 and 3 comprises a first measuring unit 20 and a second measuring unit 21 which are identical to the single measuring unit shown in FIG. 1. The wave guides of these two measuring units are fixed by welding to the wall of the conduit 1 in such manner that the corresponding measuring paths 22 and 23 of the units 20 and 21 respectively are located in two sections of the conduit 1 separated by a certain length of conduit. These measuring paths are moreover oriented at 90° to each other. It will be clear that a common processing unit may be used for the two measuring units or paths. In the case of a concentration of bubbles in a part of the conduit, the detection will obviously be better by effecting the scanning along two diameters and at two different places lengthwise of the conduit. The number of measuring units or paths disposed angularly with respect to each other and spaced apart lengthwise of the conduit could of course be multiplied so as to increase the sensitivity and the reliability of the detection.

Figure 5:
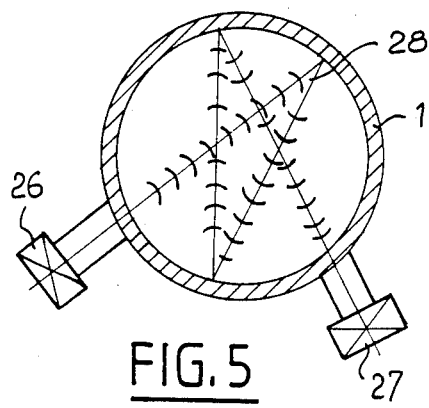
FIG. 5 is a cross-sectional view of a conduit for a liquid metal provided with a modification of the device according to the invention.

It is also possible, as shown in FIG. 5, to dispose the two detectors 26, 27 in a non-aligned configuration. The wave train 28 transmitted by the first detector 26 is reflected a plurality of times on the inner wall of the conduit 1 and thus scans a large part of the section before being received by the second detector 27. In this case, the wave guides must not be oriented along a diameter of the conduit 1.

Further, as the frequency permitting the obtainment of the best detection sensitivity depends on the size of the bubbles, it may be of interest, in the case of the device shown in FIGS. 3 and 3a to feed each of the successive units, such as 20 and 21, in such manner as to obtain a different frequency for each of the successive measuring paths 22 and 23.

When a single measuring unit is used, it may be of interest, for the same reason, to feed this unit in such manner as to obtain a frequency of the ultrasonic waves which varies with respect to time. This variation may be continuous or incremental with periodic returns to a given value.

When the source of gas introduced into the liquid metal is known, for example in the case of a steam generator in the secondary circuit of a fast neutron nuclear reactor, the placement of the detecting units will be effected by disposing a first unit upstream of the steam generator, i.e., in the sodium inlet conduit leading to the generator, and a second unit downstream of the steam generator, i.e., in the sodium outlet conduit. The comparison of the attenuations measured at the inlet and outlet of the steam generator will permit a reliable determination of the presence of a leakage in the event of a difference which is substantially greater than a predetermined threshold between the measured attenuations.

In the case of a non-identified or uncertain source of gas, it may be of interest to place upstream of the detecting device a gas source which controls the emission of bubbles in the liquid metal. This controlled and measured emission permits a calibration of the detecting device.

FIGS. 4a, 4b, 4c and 4d show four different ways of joining by welding a wave guide 24a, 24b, 24c or 24d respectively to a conduit 1 for receiving the liquid metal.

The wave guide 24a is secured to the outer surface of the conduit 1 by a weld 25a.

The wave guides 24b, 24c and 24d extend through the wall of the conduit 1 and are secured to this wall either by a penetrating weld 25b occupying the whole of the thickness of the all, or by an exterior weld 25c, or by a butt-weld 25d between an enlarged portion of the wave guide 24d and the conduit 1.

Figure 6:
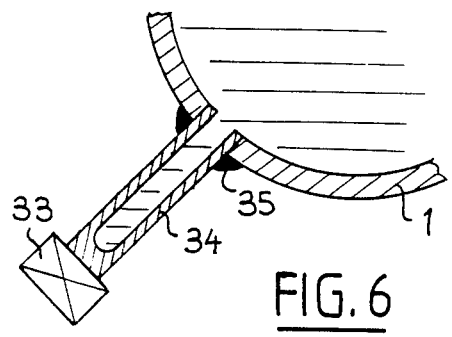
FIG. 6 is a partial cross-sectional view of a liquid metal conduit on which a hollow wave guide is secured.

The conduits for liquid metals, in particular for the sodium employed in fast neutron nuclear reactors, are often made from austenitic stainless steel. When the wave guide has a part which comes into direct contact with the liquid metal, this part must also be of stainless steel in order to avoid its corrosion and to permit welding it to the austenitic stainless steel conduit. However, the propagation of ultrasonic waves is not as good in austenitic stainless steel as in carbon steel. It is then possible to make the wave guide, or at least the part of the latter which comes into contact with the liquid metal, in a hollow shape, in particular a tubular shape, as shown in FIG. 6. The liquid then fills the cavity of the wave guide 34 in contact with the detector 33. The body part of the wave guide may also be made from carbon steel, and there may be provided at the end of the wave guide which is to be joined to the conduit a stainless steel pellet which is secured to the body part of the wave guide by a heterogenous weld or by brazing.

The wave guides which may used for detecting gas bubbles in accordance with the process of the invention usually do not permit the obtainment of a beam having a large diameter. This is why it may be necessary to use plurality of measuring units in order to effect a more complete scanning of the section or of the length of the conduit. However, the shape of the ultrasonic wave beam may be modified by providing a wave guide which comes into contact with the liquid metal by a surface of varying shape. In the case of a planar surface, a parallel beam is obtained and, in the case of a rounded and concave surface, a convergent beam is obtained. In this way, it is possible to improve the detection sensitivity, depending on the localization and the path of the bubbles in the conduit.

It is therefore clear that the process and device according to the invention permit sensitive and reliable detection of gas bubbles in any liquid metal which may possibly be at very high temperature.

There may be envisaged other embodiments of wave guides and of their junction with the enclosure containing the liquid metal, and other arrangements of measuring units, along the circumference or along the length of the enclosure containing the liquid metal.

Other processes and devices for processing the signals of the ultrasonic transducers may also be contemplated for determining the attenuation of the ultrasounds.

The process and device according to the invention may be used for the detection of gas bubbles in enclosures of shapes different from that of a circular conduit in which the liquid metal flows. This process and device are applicable in the case of reservoirs or chambers containing stagnant or stationary liquid metal.

The process and device according to the invention may be employed in installations other than fast neutron nuclear reactors and in fields other than the nuclear industry. Generally, this process and device are applicable in any type of industry employing liquid metals liable to contain gas bubbles, whether this gas be of any type or the vapor of the liquid metal.

What is claimed is:

1. A process for the ultrasonic detection of gas bubbles in a liquid metal contained in an enclosure, said process comprising the steps of
    (a) sending an ultrasonic beam into the liquid metal from a transmission point located outside the enclosure and at a given distance from the enclosure so as to cause the propagation of ultrasounds a given distance through the liquid metal;
    (b) detecting the ultrasonic beam outside the enclosure and at a given distance from the enclosure after the beam has travelled through the liquid metal;

(c) comparing the amplitude of detected ultrasonic waves with amplitude of transmitted ultrasonic waves so as determine an attenuation of the ultrasonic wave beam produced by passage through the liquid metal; and (d) deducing the presence of gas bubbles in the liquid metal if the attenuation of the ultrasonic wave beam exceeds a given threshold either continuously or in brief pulses.

2. A process according to claim 1, wherein the frequency of the ultrasonic waves is higher than 20 kHz.

3. A process according to claim 2, wherein the frequency of the ultrasonic waves is between 100 kHz and 10 MHz.

4. A process according to claim 1, wherein the frequency of the ultrasonic waves varies with respect to time.

5. A process according to claim 4, wherein the frequency of the ultrasonic waves varies in an incremental manner with a periodic passage at at least one predetermined frequency.

* * * * *